(12) United States Patent
Huntley et al.

(10) Patent No.: US 7,770,322 B2
(45) Date of Patent: Aug. 10, 2010

(54) CONTINUOUS-BATCH HYBRID PROCESS FOR PRODUCTION OF OIL AND OTHER USEFUL PRODUCTS FROM PHOTOSYNTHETIC MICROBES

(75) Inventors: Mark Edward Huntley, Kailua-Kona, HI (US); Donald G Redalje, Diamonhead, MS (US)

(73) Assignee: HR Biopetroleum, Inc., Honolulu, HI (US)

( * ) Notice: Subject to any disclaimer, the term of this patent is extended or adjusted under 35 U.S.C. 154(b) by 578 days.

(21) Appl. No.: 10/582,029

(22) PCT Filed: Jun. 7, 2006

(86) PCT No.: PCT/US2006/022443
§ 371 (c)(1),
(2), (4) Date: Jun. 7, 2006

(87) PCT Pub. No.: WO2007/013899
PCT Pub. Date: Feb. 1, 2007

(65) Prior Publication Data
US 2008/0118964 A1    May 22, 2008

(51) Int. Cl.
*A01G 7/00* (2006.01)
*C02C 1/00* (2006.01)
*C12P 5/00* (2006.01)

(52) U.S. Cl. .......................... 47/1.4; 210/602; 435/166; 435/243; 435/244; 435/257.1; 435/258.4; 435/292.1

(58) Field of Classification Search .................. None
See application file for complete search history.

(56) References Cited

U.S. PATENT DOCUMENTS

| | | | |
|---|---|---|---|
| 3,546,812 A | 12/1970 | Kobayashi et al. | |
| 3,763,824 A | 10/1973 | Schoon | |
| 4,065,875 A | 1/1978 | Srna | |
| 4,087,936 A | 5/1978 | Savins et al. | |
| 4,236,349 A * | 12/1980 | Ramus | 47/1.4 |
| 4,417,415 A * | 11/1983 | Cysewski et al. | 47/1.4 |
| 6,287,852 B1 * | 9/2001 | Kondo et al. | 435/292.1 |
| 6,558,548 B2 * | 5/2003 | Svirklys et al. | 210/603 |
| 6,579,714 B1 * | 6/2003 | Hirabayashi et al. | 435/292.1 |
| 2002/0034817 A1 * | 3/2002 | Henry et al. | 435/257.1 |

FOREIGN PATENT DOCUMENTS

| | | |
|---|---|---|
| DE | 43170064 | 11/1994 |
| WO | WO01/74990 A1 | 10/2001 |
| WO | WO2004/009826 A2 | 1/2004 |

OTHER PUBLICATIONS

Nelson et al, "Evaluation of microalgal clones for mass culture in a substropical greenhouse bivalve hatchery: Growth rates and biochemial composition at 30 degree C" 1992 vol. 106 (3-4) Abstract pp. 357.*
Stein, Janet R., Handbook of Phycological Methods Culture Methods and Growth Measurements, Cambridge University Press 1973, Press Syndicate of Cambridge, New York, NY, USA and Melbourne 3206, Australia, pp. 303-306.
Baars, J.W.M., Autecological Investigations On Marine Diatoms. 2. Generation Times of 50 Species, Aquatic Ecology, vol. 15. No. 3/Dec. 1981, Springer Netherlands, pp. 137-151.
Eppley, Richard W., Temperature and Phytoplankton Growth in the Sea, Fishery Bulletin, vol. 70, No. 4, 1972, pp. 1063-1085.
Johansen, Jeffrey R.; Barclay, William R. and Nagle, Nicholas, Physiological Variability Within Ten Strains of *Chaetoceros muellers* (Bacillariophyceae), J. Phycol, 26, (1990), pp. 271-278.
Brand, L.E. and Guillard, R.R.L., The Effects of Continuous Light and Light Intensity on the Reproduction Rates of Twenty-Two Species of Marine Phytoplankton, J. exp. mar. Biol. Ecol., 1981, vol. 50, pp. 119-132, Woods Hole, MA, USA.
Gedde, Anne Dorte, *Thalassiosira andamanica* Sp. Nov. (Bacillariophyceae), A New Diatom From The Andaman Sea (Thailand), J. Phycol. 35, (1999), pp. 198-205.
Sarthou, Geraldine; Timmermans, Klaas R.; Blain, Stephane and Treguer, Paul, Growth physiology and fate of diatoms in the ocean: a review, Journal of Sea Research 53 (2005), pp. 25-42, The Netherlands.

(Continued)

*Primary Examiner*—Herbert J. Lilling
(74) *Attorney, Agent, or Firm*—Martin E. Hsia

(57) ABSTRACT

A process for cultivating photosynthetic microbes comprising Closed Systems for continuous cultivation and Open Systems for batch cultivation, in which (a) the Closed System Area occupies no more than 20% of the Total Land Area of the cultivation facility; (b) batch cultures in the Open Systems are initiated with an inoculum from the Closed Systems containing a cell biomass of no less than 5% of the carrying capacity of said Open System; (c) the doubling rate of said photosynthetic microbe is no less than once every 16 hours; and (d) the residence time of the batch culture in said Open System is no more than a period of 5 days.

14 Claims, No Drawings

OTHER PUBLICATIONS

Lourenco, Sergio O.; Barbarino, Elisabete; Mancini-Filho, Jorge and Schinke, Katya P. and Aidar, Elizabeth, Effects of different nitrogen sources on the growth and biochemical profile of 10 marine microalgae in batch culture: an evaluation for aquaculture, Phycologia (2002), vol. 41 (2) pp. 158-168, Sao Paulo, SP, Brazil.

Strzepek, R.R., Price, N.M., Influence of irradiance and temperature on the iron content of the marine diatom *Thalassiosira weissflogii* (Bacillariophyceae), Marine Ecology Progress Series (2000), vol. 206: pp. 107-117.

Stramski, Dariuszi; Sciandra, Antoine and Claustre, Herve, Effects of temperature, nitrogen, and light limitation on the optical properties of the marine diatom *Thalassiosira pseudonana*, Limnol. Oceanogr., 47(2) 2002, pp. 392-403.

Thompson, Peter, The Response of Growth and Biochemical Composition to Variations in Daylength, Temperature, and Irradiance in the Marine Diatom *Thalassiosira pseudonana* (Bacillariophyceae), J. Phycol., 35 (1999), pp. 1215-1223.

Thompson, Peter A.; Harrison, Paul J. and Parslow, John S., Influence of Irradiance on Cell Volume and Carbon Quota for Ten Species of Marine Phytoplankton, J. Phycol, 27 (1991), pp. 351-360.

Thompson, Peter A.; Guo, Ming-Xin and Harrison, Paul J., Effects of Variation in Temperature. I. On the Biochemical Composition of Eight Species of Marine Phytoplankton, J. Phycol, 28 (1992), pp. 481-488.

\* cited by examiner

CONTINUOUS-BATCH HYBRID PROCESS FOR PRODUCTION OF OIL AND OTHER USEFUL PRODUCTS FROM PHOTOSYNTHETIC MICROBES

TECHNICAL FIELD

This invention relates to a process for producing oils and other useful products from photosynthetic microbes. The process preferably utilizes large point sources of carbon dioxide caused by industrial or resource extraction practices, such as stack gas from fossil-fuel (coal, oil and gas) burning power plants, thus reducing their emissions of carbon dioxide. The process produces, useful products, including renewable fuel—plant oils that can be directly made into liquid transportation fuel such as biodiesel.

The process is potentially very significant—for both reducing global emissions of carbon dioxide, and for producing biomass feedstocks as a starting material to manufacture fuels and other useful products that are now made primarily from geopetroleum. First, fossil-fuel burning power plants are now responsible for about one-third of the world's emissions of carbon dioxide—a so-called "greenhouse gas" that scientists believe is primarily responsible for global warming. Major point sources of carbon dioxide waste product include (i) stack gases from a variety of industrial practices such as the production of chemicals and refining of oil and gas, and (ii) collateral emissions created by the geological extraction of oil and natural gas. Second, the process described here employs microscopic plants to directly use the very same carbon dioxide waste product created by burning fuels to create yet more fuel, or to use the carbon dioxide waste product created by chemical production to create yet more chemicals. Most importantly, the use of microscopic plants in this process makes it possible to use stack gases before they are emitted into the atmosphere—a feat that cannot be accomplished by terrestrial plants—and thus reduces atmospheric emissions.

One of the main reasons that photosynthetic microbes are superior to terrestrial plants as a source of feedstock for biofuels and biologically-based chemical products is that they are approximately 10 times more productive, per unit area. Low productivity of terrestrial plants is a major bottleneck in the production of biofuels, because feedstock material must be transported to bioprocessing plants for such large distances that the amount of fuel consumed by transportation alone can easily exceed the amount of biofuel produced, thus limiting the economically practical size of the bioprocessing plant. By using photosynthetic microbes, which are about 10 times more productive, bioprocessing plants can have about 10 times greater capacity because the cost and fuel consumption of transporting the biomass feedstock (the microbes) is reduced.

Power plant stack gases typically contain in the range of 5% to 15% carbon dioxide, depending upon whether they are burning oil or coal, respectively. Stack gas wastes from industrial production processes contain comparably large amounts of carbon dioxide, and waste streams generated during resource extraction may consist of almost pure carbon dioxide. All plants use carbon dioxide and Microscopic plants live in an aquatic medium, and can withstand—indeed often require—carbon dioxide concentrations of 5% or more. Terrestrial plants, on the other hand, live in a gaseous medium (the Earth's atmosphere), which currently has a carbon dioxide concentration of about 0.035%, and cannot withstand the hundred-fold higher concentrations found in stack gases.

Specifically, this invention relates to a two-stage cultivation process, the "continuous-batch hybrid process," wherein aqueous cultures of photosynthetic microbes (single-cell organisms, including bacteria, cyanobacteria, and algae) are maintained in a state of continuous exponential growth under nutrient-sufficient conditions in a closed photobioreactor, from which a fraction is periodically removed to inoculate a batch culture in an open cultivation system where initial conditions of high light intensity and high nutrient concentrations favor continued exponential growth for a brief period, but wherein nutrients are rapidly exhausted and light becomes the limiting factor due to the proliferation of cells—conditions that favor oil biosynthesis, resulting in higher cellular oil content. "Nutrients," as defined here, are comprised of the so-called "Macronutrients," which are compounds of nitrogen and phosphorus that are generally supplied in large quantities and are the main food for growth, and the "Micronutrients," which include vitamins and compounds containing trace metals like iron or magnesium that are generally supplied in very small quantities. Overall, the continuous-batch hybrid process yields higher oil productivity than can be attained by a single stage process, either continuous or batch. Additionally, the invention provides a methodology for the reliable use of open cultivation systems, which require far less skill and experience to operate than closed systems, but which have proven otherwise unreliable for large-scale cultivation.

Photosynthetic microbes are single-celled plants that, like their multicellular (differentiated cells that are unable to survive independently) terrestrial counterparts, produce biomass that can be converted into fuels and other useful products that are now derived almost exclusively from non-renewable fossil fuels. Indeed, the fossilized ancestors of these photosynthetic microbes are the dominant source of today's geological reserves of coal, oil and gas. The biomass of today's photosynthetic microbes represent a renewable feedstock for a variety of products that include, but are not limited to oils, lubricants, plastics, petrochemicals, and fuels. Photosynthetic microbes are potentially a much better source of these products than terrestrial plants because they have higher photosynthetic efficiency, grow about ten times faster, and thus produce more biomass per unit area.

The oil content of photosynthetic microbes is generally greatest under conditions that favor low growth rates. Conditions that favor high growth rates and the highest oil content are mutually exclusive. Any process that would yield both high growth rates and high oil content in the shortest time would clearly yield the highest overall rate of oil production. However, conditions that favor high growth rates generally favor the highest content of protein.

BACKGROUND ART

Thousands of species of photosynthetic microbes are routinely cultivated at relatively small scale in the laboratory, in culture vessels ranging from several milliliters up to a few hundred liters in capacity. However, attempts to cultivate at larger scales, generally necessary for commercial production, have proven successful for fewer than 10 species—despite a worldwide effort that has lasted half a century and consumed billions of dollars.

There are two basic types of culture vessels that have been employed in the effort to cultivate photosynthetic microbes at commercial scale: (1) Photobioreactors (Closed Systems), and (2) Open Systems.

(1) Closed Systems are characterized primarily by the provision of means to control access to the atmosphere. Gas exchange with the atmosphere is allowed to occur under controllable conditions. Carbon dioxide enters the culture vessel as a fuel for growth, and oxygen, the gaseous waste product of photosynthesis, is permitted to escape the culture vessel. (The carbon is assimilated into plant biomass, and the "dioxide"—oxygen—is expelled.) However, gas exchange occurs through filtration mechanisms that are designed to prohibit entry into the culture vessel of any species of photosynthetic microbe other than the one that is being preferentially cultivated therein.

Closed Systems are usually also designed to allow for the control of other environmental conditions. The provision for control of environmental variables such as temperature, pH, nutrient concentrations, and light makes it possible to optimize growth conditions for different species of microbial plants, which, like terrestrial plants, have distinct preferences for unique combinations of such variables.

For a given set of environmental conditions, all species of photosynthetic microbes grow at their maximum rate within a narrow range of cell concentrations. Accordingly, some Closed Systems are designed to operate as "turbidostats," wherein the optical property of turbidity (opaqueness), which is a function of cell concentration, is monitored by means of programmable sensors that measure the optical density of the medium. The operator may specify a desired range of acceptable cell concentration, between a low value and a high value. The low value corresponds directly to a specific low optical density (the "low set point"), and the high value to a specific high optical density (the "high set point"). The optical density sensor is then programmed accordingly. When optical density attains a value that exceeds the designated upper set point, the turbidostat activates a control mechanism that provides for removing (harvesting) a fraction of the culture and replacing it with cell-free nutrient medium, thereby diluting the cell concentration to yield a value of optical density that matches the designated lower set point. The cells then will grow, increasing in concentration until optical density attains a value that once again exceeds the upper set point, at which time the cycle repeats.

Preferably a Closed System culture vessel is constructed primarily of transparent material, such as glass or plastic, that allows the transmission of photosynthetically active radiation (visible light), but which otherwise separates the culture medium from the atmosphere. Culture vessels may take many different shapes, but they all share in common one spatial dimension that limits their performance, and that is their depth relative to incident light intensity. This feature arises from a basic property of photosynthesis, namely, that photosynthetic rate is limited by light intensity. Thus, at any given light intensity, the rate of photosynthesis of a cell culture is maximized as a function of the Lighted Area, i.e. the area of the culture medium that is exposed to light (not necessarily the Surface Area, which may include areas of the culture vessel that are not exposed to light). Consider two culture vessels, both outdoors and exposed to sunlight. One is in the shape of a rectangular pond with solid sides and bottom, and the second is in the shape of a transparent cylinder, placed horizontally on top of the ground. For the rectangular pond the Surface Area includes the top, bottom, and sides of the pond, but only the top area of the culture medium is exposed to sunlight. For such an outdoor pond, then, the Lighted Area is equal to less than half the Surface Area. By comparison, for the transparent cylinder, the Surface Area is the entire surface of the cylinder and, no matter what the time of day, half of the Surface Area will always be directly illuminated by sunlight. Thus, for the cylinder, the Lighted Area is equal to half the Surface Area A second factor affecting the relationship between photosynthesis and light is the cell concentration in the culture medium. The greater the cell concentration within a medium, the less the depth to which light may penetrate, because light penetration decreases approximately exponentially as a function of cell concentration. In other words, if the cell concentration increases at a constant rate, light disappears faster and faster. At some depth in a cell culture, then, light will actually decrease to zero.

As a practical matter, the optimal culture depth for photosynthetic microbes exposed to full sunlight is generally in the range of 10 to 20 centimeters. No advantage can be gained by providing greater depth of the culture, because the concentration of cells per unit Lighted Area will remain the same, and deeper cells will not receive enough light. The optimal depth, then, puts a limit on the normal operating capacity of any culture system, regardless of its Lighted Area. This phenomenon is a critically important feature in the design of cultivation systems. Greater volumes require more materials, at greater cost, but at some point the increase in volume provides no increase in productivity per unit Lighted Area.

Cultures of photosynthetic microbes generally require stirring or mixing in order to maintain a homogeneous distribution of cells in the medium. The natural tendency of photosynthetic microbes in still water is to form dense aggregations, within which the properties of the medium are altered to the detriment of the culture. On a microscale, within the aggregation, the availability of light and the concentration of nutrients and gases become so different from the remainder of the medium that growth is limited. Some species have appendages known as cilia or flagellae that allow them to swim; such motile ("moving") species actively form aggregations. Most non-motile species are heavier than water and will sink, forming a passive aggregation on the bottom. To prevent such aggregations, Closed Systems must provide a means for creating turbulence using devices such as airlifts or pumps.

(2) Open Systems differ from Closed Systems in one critical feature, namely that they are open to the atmosphere. This feature is advantageous to both construction and operation, in several ways. First, because the Lighted Area of an Open System is exposed directly to sunlight, there is no requirement to use a transparent material to construct the culture vessel; this affords broad latitude in the choice of materials. Second, because no material is used to cover the Lighted Area of the Open System, the amount and cost of material is reduced by about half. Third, Open Systems are generally easier to clean than Closed Systems. Over time the inner surface of any culture vessel will tend to accumulate a film of microbial growth. In a Closed System the accumulation of such a film on the Lighted Area will absorb light; the consequent decrease in light intensity causes a decrease in productivity. In both Open Systems and Closed Systems the culture vessel surface can accumulate microbial films of undesirable species that may be detrimental to growth and production of the desired species. In either case, the culture vessel surface will require cleaning from time to time. As a practical matter, Open Systems allow a much wider choice of cleaning methodologies. For example, people and large types of mechanical cleaning equipment such as hoses, pressure washers, and scrubbers that cannot enter the confined space of a Closed System can easily enter an Open System.

The principal disadvantage of an Open System is that, by being open to the atmosphere, it is susceptible to contamination by unwanted species. One may begin the operation of an Open System culture with only one desired species of photosynthetic microbe. However, undesired species will inevitably be introduced, whether by atmospheric transport or other means. Any undesired species that grows faster than the desired species in the same environmental conditions will, over time, outcompete the desired species and will ultimately dominate the culture.

In summary, Closed Systems are designed specifically to prohibit contamination by undesired species, with the expectation that continuous cultivation of a desired species may be possible for a much longer period than would be possible in an Open System. However, Closed Systems are more complicated to construct and operate. Open Systems afford a wider choice of materials for construction, and also afford a wider choice of cleaning methodologies. Closed Systems require additional operating practices, such as the use of sterile technique during fluid transfers, which call for greater time and expertise on the part of the operator.

Theoretical differences between Closed Systems and Open Systems have been borne out in practice. The first photosynthetic microbe was isolated from nature and grown in pure culture little more than a hundred years ago, but it was not until the late 1930s that sufficiently large volumes of a single species could be cultivated to permit chemical analysis. By the 1940s various species were being grown in laboratory cultures of about 25 liters, and it was discovered that, by altering environmental conditions of the culture, either the oil or protein content of some species could be made to exceed 60% of the total cell mass.

The first attempts at large-scale cultivation began in the 1950s, stimulated by widespread interest in photosynthetic microbes as a source of cheap protein for foods and animal feeds. The first Open Systems, built in Germany, took the shape of shallow, elongated, recirculating raceways, with flow provided by a paddlewheel device. Nationally-funded programs developed rapidly throughout the world, all following the German "open pond" design. The first open ponds had capacities of just a few thousand liters. By the late 1950s, capacities of almost 100,000 liters had been attained and, by the late 1960s, almost 1,000,000 liters. Such increases in capacity brought economies of scale.

Hundreds of species were tested in the laboratory, and attempts were made to grow the best protein producers in open ponds during the 1960s and 1970s. Only a few species proved to be amenable to sustained cultivation. These few species, such as *Spirulina platensis* and *Dunaliella salina*, went on to become the basis of commercial production, effected in open pond systems covering hundreds of acres. The successful commercial species proved to be "extremophiles," which thrive in conditions of unusually high pH or salinity. Most species prefer conditions that prevail in nature, where numerous species thrive simultaneously. For two decades, all attempts to cultivate single-species cultures of non-extremophiles in open ponds failed after less than a few months because they were contaminated by other species that thrived under the same environmental conditions.

Renewed interest in large-scale cultivation was stimulated in the 1980s and 1990s by the prospect of producing renewable biofuels using oils from photosynthetic microbes as a feedstock. During this period government agencies of the USA and Japan, for example, invested approximately $150 million in such an effort. Such programs shared two goals: first, to collect and identify species of photosynthetic microbes that produce high concentrations of oil and then to determine the environmental conditions under which they do so; and, second, to design and demonstrate the operation of large-scale cultivation systems for the production of biofuel feedstocks using species that had been developed in the laboratory. Both programs succeeded at the first goal, but failed at the second.

Laboratory studies quantified earlier findings. Culture collections of hundreds of species were amassed. Research on numerous strains demonstrated that, in general, nitrogen sufficiency (nitrogen is needed for protein synthesis) promoted high growth rates and low oil content, whereas nitrogen deficiency resulted in low growth rates and high oil content. For some species, it has also been noted that stress, caused by factors such as high light intensity or very high temperatures, can induce species to shift from protein synthesis to oil synthesis. Species capable of optimal oil production—the highest oil content at the highest growth rate—were selected for large-scale production trials.

Large-scale production was once again attempted in the late 1980s and early 1990s using open pond systems. Operating results were similar to those obtained for the three previous decades. Promising oil-producing species were selected from the collections, and cultures were inoculated into the ponds. However, as in prior experience, single-species cultures could not be maintained for more than a few weeks or months. The final report of the US program referred to this phenomenon as an "uncertainty with the nature of species control achieved."

By the 1990s the status of large-scale cultivation had not progressed beyond the point reached in the 1960s. Three types of microalgae—*Spirulina*, *Dunaliella* and *Chlorella*—were being cultivated at facilities using open pond systems covering more than 100 acres. Scores of other species had been attempted worldwide, but all attempts had failed. The biofuels programs, in particular, had been unable to grow any desired species at any scale outside the laboratory. Moreover, the biofuels programs had focused on attempts to demonstrate the highest possible biomass production rates under nutrient-sufficiency, conditions that are known from laboratory studies to favor low oil content. No attempts were made at large-scale to maximize oil production.

Large scale Closed System technology began to receive significant attention in the early 1990s, once it became evident that cultures of most species exposed to atmosphere were not sustainable. At that time, the largest Closed Systems that had ever been used were no more than a few thousand liters in capacity. Advances in the past decade have succeeded at increasing reactor capacity by a factor of about 10, to about 30,000 liters. But this is nowhere near the rate of increase achieved for Open System capacity that, also over a decade (in the 1950s to 1960s), increased by a factor of 1,000.

The upper limit of Closed System capacity is, in large part, a direct consequence of inherent design requirements. All basic Closed System designs in use today were first developed in the 1950s, and may be categorized as follows: (1) vertical bags, tubes, or towers; (2) flat-plate reactors; and (3) horizontal tubes. Vertical systems are constrained by height limitations. Even when exposed to full sunlight, most cultures achieve such high cell densities that light is almost entirely absorbed at a distance of more than 15 to 20 cm from the Lighted Area. This constraint limits the diameter of the culture vessel to no more than 30 or 40 cm. To achieve a capacity of more than 10,000 liters, for example, a 40-cm diameter vertical system would have to be more than 80 meters (260 feet) high. Such dimensions present clear challenges in structural engineering which, even if achievable, become increasingly complex the greater the volume of the system. One of the obvious solutions has been to introduce an illumination system within the reactor, but experience has shown that this introduces other problems, of which bio-fouling may be the greatest. Over a relatively short time, the surface of the light source tends to become covered with a microbial film, sharply reducing light intensity and thus defeating the purpose of the light source. Removing the culture and cleaning the vessel is one option, but hardly desirable if the goal is sustained operation. Another common anti-fouling option, making the surface of the light source toxic to microbes, is clearly undesirable. In general, the use of internal illumination makes the system more complex.

Horizontal systems such as flat-plate reactors and horizontal tubes eliminate the need for the structural engineering required of vertical systems. Using the earth's surface for structural support, the potential capacity of such systems might appear limitless. However, the capacity of horizontal systems is generally limited by the requirement for turbulent flow, whether used to maintain adequate mixing or to fill and empty the culture vessel.

Turbulent flow in a pipe or a channel is described by the Reynolds number, defined as the velocity of the fluid multiplied by the "characteristic length" of the pipe or channel, and divided by the viscosity of the fluid. The Reynolds number does not have any units, like inches or pounds, and is therefore "dimensionless," like "one-half" or "two-thirds". The characteristic length of a fluid-filled pipe is its diameter; the characteristic length of a wide channel is its depth. For a fluid of constant viscosity, flow will become increasingly turbulent as the velocity of flow increases. Turbulence also increases in proportion to the characteristic length; this happens because pipe and channel surfaces are "sticky." Surfaces cause friction that slows down the flow; the flow rate is almost zero next to the surface, and increases with distance away from the surface. Thus, in a pipe or channel with small characteristic length, the surface friction will have a great effect on the average flow. By contrast, in a pipe or channel with large characteristic length, the surface friction will have little effect on the average flow, and turbulence will be greater.

Surface friction also adds up over distance. Imagine a very long pipe through which water is propelled by a pump. At the origin, near the pump, the flow is turbulent. The farther the fluid moves down the pipe, the more surface it is exposed to and, the more surface it is exposed to, the more its flow is slowed by friction. At some point from the origin, the accumulated friction has removed so much energy from the fluid flow that it ceases to be turbulent. This happens when the Reynolds number falls below a value of about 2000, and then the flow is said to be "laminar."

Laminar flow is not desirable in cell cultures because in such conditions the cells have a tendency to aggregate, either by sinking or swimming. Turbulent flow prevents such aggregations. Imagine, for example, how sand particles would rapidly sink to the bottom in a still pond, but would not do so in a large breaking wave or a rapidly moving stream.

In summary, then, turbulent flow is maintained by avoiding very low fluid velocities, very small characteristic lengths, and very long channels. The characteristic length for horizontal Closed Systems such as flat-plate reactors or horizontal tubes is the depth of the culture, which, as explained previously, has a practical upper limit of about 20 cm. One can create turbulent flow in a flat-plate reactor or a horizontal tube with any number of devices such as pumps or airlifts. However, with increasing distance from the origin of the flow, turbulent energy is lost to friction such that, at some finite distance flow becomes laminar. In laminar flow conditions the cells of most photosynthetic microbes will sink to the bottom of the reactor. This is undesirable for many reasons, not the least of which is that harvesting the cells becomes problematical. One solution is to provide more turbulent energy at the source, but this is acceptable only to an upper limit where mechanical shear damages the cells themselves. Yet another solution is to provide multiple pumps, for example, throughout the reactor, but this approach introduces additional complexities of both construction and operation.

As a matter of practice, vertical Closed Systems are limited to a capacity of less than about 1,000 liters, and horizontal Closed Systems appear to be limited to capacities less than about 50,000 liters. For the purpose of large-scale cultivation of photosynthetic microbes, Closed Systems are much more costly and complex to construct and operate than Open Systems. This is because each independent system requires its own independent infrastructure: a set of devices or mechanisms for providing turbulent mixing, introduction and removal of medium, and monitoring and control of variables such as pH and temperature. To cover a given area of land with Closed Systems requires at least 10 times more infrastructure than covering the same area of land with Open Systems, rendering Closed System cultivation much more complicated.

In practice, every cultivation system for photosynthetic microbes involves a coupling of both Open Systems and Closed Systems at some scale. All cultivation systems, regardless of scale, ultimately depend for their original inoculum of cells on culture collections routinely maintained around the world. All culture collections exclusively maintain their cell cultures in Petri dishes, test tubes, or sterilized flasks—all of which are, strictly speaking, Closed Systems. Even large-scale production systems that might be considered to consist "purely" of Open Systems must rely ultimately on a Closed System to supply the original inoculum.

The main technical conundrum for the production of photosynthetic microbes is that Open System technology has advanced to a large scale that is economical and relatively easy to operate, but cannot provide sustainable production of desired microbes. By contrast, Closed Systems do provide sustainable production of desired microbes, but even at their largest scale they are costly and complicated to operate.

Thus, there is a need for a production method that provides for sustainable production by reducing the potential for contamination and yet does not substantially increase the complexity or cost of construction or operation.

It is therefore an object of this invention to provide an effective method for sustainable production of photosynthetic microbes at large scales that may be easily constructed and does not increase the complexity or cost of construction or operation.

It is a still further object of this invention to provide a method of production that is especially suited to optimizing the production of oils and other useful products from photosynthetic microbes. Oils and other useful products may then be extracted and purified from the aggregate biomass by means of a variety of chemical methods.

SUMMARY OF THE INVENTION

These and other objects are achieved by a two-stage, continuous-batch production methodology, wherein the first stage of continuous production is accomplished in Closed Systems and the second stage of batch production is accomplished in Open Systems. First, one must select (including creating by, for example, genetic modification) a microbe that is capable of growing at a rate of at least one doubling every 16 hours, when supplied with sufficient carbon dioxide, provided that light and nutrients are adequate. Such genetic modification is disclosed, for example, in "Transgenic microalgae as green cell-factories," by R. León-Bañares, D.

González-Ballester, A. Galván and E. Fernández (in *Trends in Biotechnology*, Volume 22(1), pp. 45-52, 2004), which is incorporated herein by reference. For example, it is presently preferred to practice this invention with the following species and/or strains: (i) *Tetraselmis suecica*, "TETRA1" strain in the University of Hawaii Culture Collection; *Isochrysis galbana*, "ISOCH1" strain in the University of Hawaii Culture Collection; (iii) *Phaeodactylum tricornutum*, either strain "PHAEO1" or "PHAEO2" in the University of Hawaii Culture Collection; or (iv) *Nannochloropsis* sp., in particular the A. Sukenik strain used by Fabregás et al. (2004), reported in "The cell composition of *Nannochloropsis* sp. changes under different irradiances in semicontinuous culture," World Journal of Microbiology and Biotechnology, Vol. 20, pp. 31-35. The University of Hawaii Culture Collection includes the entire culture collection of several hundred species and strains amassed in the 1980s and 1990s by the U.S. Natural Renewable Energy Laboratory (NREL), specifically for the purpose of producing biofuels from photosynthetic microbes. Additional species that might also be used include *Dunaliella primolecta* and *Nitzschia closterium*. In particular, Closed Systems should comprise no more than 20% of the Total Land Area of cultures, i.e. the total area occupied by the Closed System Area plus the Open System Area. Furthermore, given that every species of photosynthetic microbe attains a maximum biomass per unit Lighted Area under a given set of environmental conditions (the "carrying capacity"), the amount of biomass provided by the Closed Systems to initiate or "inoculate" any Open System culture should be equal to more than 5% of the carrying capacity of the Open System. To maximize the carrying capacity of the Open System cultures, they should be provided with sufficient nutrients so that light, not nutrients, limits the carrying capacity. Additionally, no batch culture in any Open System should be allowed to persist for a period (the "residence time") of more than 5 days.

The limitation of 20% of the Total Land Area occupied by the Closed System Area assures that the complexity of construction and operation of the entire production facility is minimized. The provisions for the minimum biomass inoculum and the maximum residence time assure that the risks of contamination of the Open System cultures by undesirable species are so reduced as to be inconsequential. This process may be used for any species of photosynthetic microbe that meets the growth rate requirements stated above.

DESCRIPTION OF A PREFERRED EMBODIMENT

It is preferred that the Total Land Area in active cultivation at any production facility be comprised of no more than 20% Closed System Area and no less than 80% Open System Area. The calculation of the Open System Area for this purpose means only the Lighted Area of culture medium in the Open Systems, assuming that all Open Systems in the production facility contain culture medium. The calculation of the Closed System Area, however, includes both the "Plan Area" covered by the reactors and also any "Inert Area" between adjacent reactor vessels. Imagine, for example, an area of land occupied by a series of horizontal tubular Closed Systems. The Plan Area will be covered by the reactors themselves (e.g. a 10 foot long tube, 1 foot in diameter, covers an area of 10 square feet), and is equal to the Lighted Area of the culture medium, but there may be additional Inert Area between adjacent tubes that is not covered by reactors. The entire area of land required by the Closed Systems, i.e the Closed System Area, is the Plan Area plus the Inert Area. By analogy, the entire area of this page is required for writing, but the writing itself occupies only a fraction of the total area on the page.

The provision for 20% Closed System Area and 80% Open System Area assures greater efficiency because the overall complexity of construction and operation of any production facility is substantially reduced by comparison to a facility that would be comprised entirely of Closed Systems.

It is preferred that (1) the amount of biomass provided by the Closed Systems to inoculate the Open Systems should be equal to more than 5% of the carrying capacity of the aggregate Open Systems; (2) the growth rate of the species being cultivated is greater than approximately one and a half doublings per day (i.e. cell biomass doubles about every 16 hours); and that (3) no culture be maintained in any Open system for a period of more than 5 days. The combination of these three limitations assures that, under any circumstances, the culture should attain a biomass of the desired microbe that is equal to at least approximately 90% of the carrying capacity in 5 days or less. This is important for several reasons. First, a culture that is inoculated at a relatively high cell concentration (i.e. greater than 5% of carrying capacity) will dominate the medium compared to any unwanted cells that may have inadvertently been introduced. Second, because most species grow at rates substantially less than 1 doubling every 16 hours (1.5 doublings per day), a species that is capable of growing this rapidly will outpace most potential competitors. Third, the combination of the large inoculum (greater than 5% of carrying capacity) and high growth rate (greater than 1 doubling every 16 hours) assures that, within 5 days, the total biomass will be very near carrying capacity. These conditions are important to (1) reducing the risk of contamination, and (2) promoting the production of total biomass or the biosynthesis or production of oil. First, a potential contaminant would have to have a large inoculum and would have to grow more rapidly than the desired species to dominate the culture medium within 5 days. Second, oil production in particular is favored in cultures that are near carrying capacity because resources become limiting to growth once the culture passes 50% of carrying capacity. By limiting resources favorable to growth, one generally stimulates the biosynthesis of oil.

It is preferred that the cell cultures are supplied with gaseous carbon dioxide in a manner that permits the carbon dioxide to dissolve in the medium. This method not only provides a constant source of the carbon needed for growth, but also has the effect of maintaining more or less constant pH of the medium, without which the pH would tend to increase as carbon dioxide is removed, leading to unfavorable conditions for growth. Optimally, the carbon dioxide for this process is provided by point source emissions from resource extraction processes (such as drilling for oil or gas), or from industrial manufacturing processes or fossil-fuel burning power plants—all of which involve a waste stream of gas that is rich in carbon dioxide. The process described here avoids emission of the waste carbon dioxide into the atmosphere and instead converts it into potentially useful biomass.

One could improve upon the preferred conditions. Optimally, one could closely approach carrying capacity in the aggregate Open Systems within one day, which would further reduce the potential for contamination. This could be achieved by using an initial inoculum of 15% of aggregate Open System carrying capacity for a species with a growth rate of more than 6 doublings per day (equivalent to 1 doubling of cell biomass about every 4 hours). In this example, imagine that the species grows at the same rate in both Closed Systems and Open Systems, and that the species also attains the same concentration of biomass per unit area in both Closed Systems and Open Systems. Now, if Closed Systems occupy 20% of the Total Land Area, then a 15% inoculum for the Open Systems would be obtained by removing 75% of the Closed System culture (i.e. 75%×20%=15%). Using a 15% inoculum in the Open Systems, the cell biomass would double to 30% in the first 4 hours, to 60% in the next 4 hours, and in less than the next 4 hours could achieve 100% (i.e. its carrying capacity). The Closed Systems will be restored to their pre-inoculation biomass in about the same amount of time. The Closed Systems contain only 25% of their original biomass after inoculum is removed; in the first 4 hours this doubles to 50% of the original biomass, and in the second 4 hours, it doubles again, this time to 100% of the original biomass. In this example, the carrying capacity of the Open Systems is achieved within one day and, within the same day, the biomass of the Closed Systems is restored to its initial value. The highest exponential growth rate recorded for photosynthetic microbes is less than about 8 doublings per day (equivalent to 1 doubling about every 3 hours), even better results might be achieved in less time with a greater amount of initial inoculum.

The preferred method, using a species with a growth rate greater than about 1.5 doublings per day, inoculating the Open System with a biomass of at least 5% of carrying capacity, and harvesting the culture no later than 5 days after inoculation, assures a relatively high oil content. It also assures that the Open System culture will not be significantly contaminated, since decades of experience show that Open System cultures usually take more than 5 days—usually several weeks—to become contaminated by undesired species.

To practice the preferred method it is necessary to first determine the carrying capacity of the Open System. Carrying capacity for most species provided with excess nutrients in a turbulent flow environment is generally in the range of about 100 to 500 grams dry weight per square meter of Lighted Area. Variations in this range will depend primarily upon light intensity, more specifically the total daily light energy of the sun, as the limiting factor. For example, the total "irradiance" (light energy of the sun) on a sunny day is about twice as much as it is on a cloudy day. The corresponding difference in carrying capacity would be about the same, i.e. about a factor of two. Furthermore, the average irradiance is greatest in the tropics, and decreases at higher latitudes. For example, average irradiance in tropical Honolulu is about 40% greater than in New York, and about 2 times greater than in northern Alaska. Accordingly, the average carrying capacity in Alaska would only be half of that in Hawaii. The greatest irradiance of the year occurs on the longest day of the year. North or south of the tropics, this happens on the first day of summer (the summer solstice). At the equator, maximum daily irradiance happens twice a year, when the sun passes directly overhead on the first day of spring (the spring equinox) and once again on the first day of fall (the fall equinox). Elsewhere in the tropics, the maximum daily irradiance also happens twice a year, somewhere between the spring and fall equinoxes.

The carrying capacity of a system for a desired species of photosynthetic microbe should be determined empirically as follows. If Open Systems in the production facility have different dimensions, then the calculation of carrying capacity should be determined for each set of systems having different dimensions. Preferably, the determination of carrying capacity should be carried out within about 15 days of the time when daily irradiance is at its annual maximum. The Open System should be inoculated with a volume of culture provided by the Closed Systems, and the Open System filled approximately to standard operating capacity with nutrient medium. Macronutrient concentrations (i.e. inorganic nitrogen and phosphorus) should be provided in excess, defined by demonstrating that once the biomass in the Open System has reached its maximum, macronutrients will still be present in measurable concentrations (the microbes won't have eaten all the food). After inoculation, measurements of the biomass of the Open System should be made at least several times per day until such time as the biomass does not increase. The biomass at which the increase ceases is the carrying capacity. The determination should be repeated at least several times during the specified period, and the average of these determinations calculated to define the maximum carrying capacity.

The present invention has been disclosed with respect to the presently preferred embodiments described herein, but those skilled in the art will appreciate that there may be other embodiments that fall within the sprit and the scope of the invention. Thus the invention is not limited by what is described in the specification, but is only limited by the claims. For example, this invention can be practiced with different types of Open Systems and Closed Systems. Furthermore, this invention can be practiced with photosynthetic microbes with widely varying growth rates and carrying capacities, and is not limited to those species being cultivated for their oil content, but can also include species that accumulate other products of value in batch cultures, whether or not they have attained a maximum rate of biomass production or they have stopped growing.

INDUSTRIAL APPLICABILITY

This invention can be used whenever it is desired to produce any specific species of photosynthetic microbe in an Open System while avoiding substantial contamination by undesired species. The biomass thus produced from photosynthetic microbes can then be used as a renewable feedstock to manufacture products that now rely almost exclusively on feedstocks derived from fossil deposits of carbon, namely coal, oil and gas. For example, the oil fraction of photosynthetic microbes may be extracted and chemically converted to transportation fuel, such as biodiesel, or to lubricants. Alternatively, the biomass feedstock may be used in a process such as fluidized bed gasification, pyrolysis, or entrained flow gasification, from which the resulting material may be used in turn to manufacture transportation fuels such as biodiesel or dimethyl ether, or bulk chemicals such as methanol or mixed alcohols or, for that matter, any product that uses fossil fuels as a starting material or feedstock. Additionally, carbon-containing waste products from any of the above processes could yield further energy by methods such as anaerobic digestion, which produces methane (natural gas), or co-firing with other combustible fuels in a power plant to produce electricity.

What is claimed is:

1. A process for cultivating photosynthetic microbes, comprising:
    selecting a species of photosynthetic microbe capable of doubling in biomass in approximately 16 hours or less when supplied with sufficient carbon dioxide in an open system that has a carrying capacity;
    introducing said species into one or more closed systems;
    allowing said species to grow in said closed systems to a biomass that exceeds 5% of said open system's carrying capacity;
    inoculating an initial biomass of said species that is no less than 5% of said carrying capacity from said closed systems into said open system;
    supplying carbon dioxide to said open system to replace carbon dioxide removed by said microbes; and maintaining said species in said open system to double in biomass approximately every 16 hours or less for a period of less than 5 days.

2. A process according to claim 1, wherein said photosynthetic microbe is selected from the group consisting of bacteria, cyanobacteria and algae.

3. A process according to claim 1, wherein said species doubles in biomass in said open system at a rate between approximately 1.5 doublings per day and up to approximately 8 doublings per day.

4. A process according to claim 1, wherein said species doubles in biomass in said open system at a rate between at least once every 16 hours and up to once every 3 hours.

5. A process according to claim 4, further comprising removing substantially all of said species from said open system at most 5 days after said inoculating step.

6. A process according to claim 1, wherein said maintaining step is performed so that growth of said species is limited by availability of carbon dioxide.

7. A process according to claim 1, wherein said maintaining step is performed until after said species reaches approximately 90% of said carrying capacity.

8. A process according to claim 1, wherein said supplying step is performed using stack gas from a source selected from the group consisting of the burning of a fossil fuel, the industrial production of chemicals, or the extraction of fossil fuels from geological deposits of fossil fuels.

9. A process for synthesizing oil, comprising:
selecting a species of photosynthetic microbe that doubles in biomass in approximately 16 hours or less when supplied with sufficient carbon dioxide in an open system that has a carrying capacity;
introducing said species into one or more closed systems;
culturing said species in said closed systems until said species grows to a biomass that exceeds 5% of said open system's carrying capacity;
inoculating an initial biomass of said species that is no less than 5% of said carrying capacity from said closed systems into said open system;
supplying carbon dioxide to said open system to replace carbon dioxide removed by said microbes; and
maintaining said species in said open system to double approximately every 16 hours or less for a period of less than 5 days until said species attains approximately 90% of said carrying capacity;
wherein said maintaining step is carried out with high initial nutrient concentrations but limited nitrogen availability, whereby initial conditions of high light intensity and high nutrient concentrations favor continued exponential growth for a short period, but wherein growth becomes limited by nitrogen availability which inhibits protein synthesis, whereby oil content is increased.

10. A process for culturing photosynthetic microbes, comprising:
selecting a species of photosynthetic microbe that has a growth rate of at least approximately one doubling every 16 hours when supplied with sufficient carbon dioxide in an open system having a carrying capacity;
culturing said microbe in one or more closed systems;
inoculating an open system with an amount of said microbes from said closed systems equal to approximately 5% or more of said carrying capacity;
supplying carbon dioxide to said open system to replace carbon dioxide removed by said microbes;
maintaining said microbes in said open system to grow at least said growth rate; and
harvesting said microbes from said open system less than approximately 5 days after said inoculating step.

11. A process according to claim 10, further comprising:
maintaining said open system so growth of said microbes is limited by availability of carbon dioxide.

12. A process for creating biomass feedstock, comprising:
selecting a species of photosynthetic microbe that doubles in biomass in approximately 16 hours or less when supplied with sufficient carbon dioxide in an open system that has a carrying capacity;
introducing said species into one or more closed systems until said species grows to a biomass that exceeds 5% of said carrying capacity;
inoculating an initial biomass of said species that is no less than 5% of said carrying capacity from said closed systems into said open system;
supplying carbon dioxide to said open system to replace carbon dioxide removed by said species; and
maintaining said species in said open system to double approximately every 16 hours or less for a period of less than 5 days to create a biomass feedstock.

13. A process for using stack gas, comprising:
selecting a species of photosynthetic microbe that doubles in biomass in approximately 16 hours or less when supplied with sufficient carbon dioxide in an open system that has a carrying capacity;
introducing said species into one or more closed systems;
supplying said stack gas into said closed systems;
allowing said species to grow in said closed systems and to use said stack gas to grow to a biomass that exceeds 5% of said open system's carrying capacity;
inoculating an initial biomass of said species that is no less than 5% of said carrying capacity from said closed systems into said open system;
supplying carbon dioxide to said open system to replace carbon dioxide removed by said species; and
maintaining said species in said open system to double in biomass approximately every 16 hours or less for a period of less than 5 days.

14. A process according to any one of claim 1, 9, 10, 12 or 13, wherein said species is selected from the group consisting of *Tetraselmis suecica*, "Tetra 1" strain; *Isochrysis galbana*, "ISOCH1" strain; *Phaeodactylum tricornutum*, either strain "PHAEO1" or "PHAEO2"; *Nannochloropsis* sp., A. Sukenik strain; *Dunaliella primolecta*; and *Nitzschia closterium*.

* * * * *

UNITED STATES PATENT AND TRADEMARK OFFICE
CERTIFICATE OF CORRECTION

| | | |
|---|---|---|
| PATENT NO. | : 7,770,322 B2 | Page 1 of 1 |
| APPLICATION NO. | : 10/582029 | |
| DATED | : August 10, 2010 | |
| INVENTOR(S) | : Mark Edward Huntley and Donald G Redalje | |

It is certified that error appears in the above-identified patent and that said Letters Patent is hereby corrected as shown below:

In claim 10 (column 14, lines 9-10), "at least said growth rate" should be "at at least said growth rate."

In claim 14 (column 14, line 50), "claim" should be "claims."

Signed and Sealed this

Fifteenth Day of February, 2011

David J. Kappos
*Director of the United States Patent and Trademark Office*